(12) United States Patent
Patel et al.

(10) Patent No.: US 8,637,057 B2
(45) Date of Patent: *Jan. 28, 2014

(54) COSMETIC EMULSIONS CONTAINING UNCOATED SILICONE ELASTOMERS AND NON SILICONE TREATED PIGMENTS

(75) Inventors: Dhaval Patel, Edison, NJ (US); Gisela Perruna, Rahway, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,139

(22) Filed: May 29, 2012

(65) Prior Publication Data

US 2012/0237463 A1    Sep. 20, 2012

Related U.S. Application Data

(63) Continuation of application No. 11/410,465, filed on Apr. 25, 2006, now abandoned.

(51) Int. Cl.
- *A61K 8/02* (2006.01)
- *A61K 8/00* (2006.01)
- *A61K 8/18* (2006.01)
- *A61Q 1/02* (2006.01)
- *A61Q 19/04* (2006.01)

(52) U.S. Cl.
USPC .......................................... 424/401; 424/63

(58) Field of Classification Search
USPC ....................................................... 424/401
See application file for complete search history.

(56) References Cited

U.S. PATENT DOCUMENTS

| | | | |
|---|---|---|---|
| 4,268,499 A | 5/1981 | Keil | |
| 4,606,914 A | 8/1986 | Miyoshi | |
| 5,167,709 A | 12/1992 | Shinohara et al. | |
| 5,928,658 A | 7/1999 | Kishida et al. | |
| 6,296,860 B1 | 10/2001 | Hasegawa et al. | |
| 6,524,598 B2 | 2/2003 | Sunkel et al. | |
| 6,548,074 B1 | 4/2003 | Mohammadi | |
| 6,793,915 B1 | 9/2004 | Guenin et al. | |
| 2002/0028184 A1 | 3/2002 | Sunkel et al. | |
| 2002/0028223 A1 | 3/2002 | Vatter et al. | |
| 2003/0049212 A1 | 3/2003 | Robinson et al. | |
| 2003/0108498 A1 | 6/2003 | Stephens et al. | |
| 2004/0241126 A1 | 12/2004 | Sakuta | |
| 2004/0265346 A1 | 12/2004 | Verloo et al. | |
| 2005/0019284 A1 | 1/2005 | Van Leeuwen et al. | |
| 2005/0074474 A1 | 4/2005 | Sako | |
| 2005/0260148 A1 | 11/2005 | Elliott et al. | |
| 2006/0013792 A1 | 1/2006 | Fontaine et al. | |
| 2006/0013793 A1 | 1/2006 | Themens | |
| 2007/0020220 A1 | 1/2007 | Osborne | |
| 2007/0189989 A1 | 8/2007 | Cantwell et al. | |

FOREIGN PATENT DOCUMENTS

| | | |
|---|---|---|
| DE | 10200712 A1 | 7/2003 |
| EP | 1582203 A1 | 10/2005 |
| JP | 11228343 A | 8/1999 |
| JP | 11246354 A | 9/1999 |
| JP | 2000309509 A | 11/2000 |
| JP | 2003267853 A | 9/2003 |
| JP | 2004203789 A | 7/2004 |
| JP | 2006028184 A | 2/2006 |
| WO | WO-03035016 A1 | 5/2003 |

OTHER PUBLICATIONS

European Search Report, EP 07008094, dated May 26, 2010.
English Abstract of JP-11246354-A.
English Abstract of JP-2003267853-A.
English Abstract of JP-2004203789-A.

*Primary Examiner* — Layla Soroush
(74) *Attorney, Agent, or Firm* — Novak Druce Connolly Bove + Quigg LLP

(57) ABSTRACT

Disclosed are cosmetic compositions in the form of an emulsion that contain an uncoated silicone elastomer, a solvent for the elastomer, a non-silicone treated pigment and an emulsifier, methods of making the compositions, and methods of applying the compositions to a keratinous substrate or tissue.

24 Claims, No Drawings

COSMETIC EMULSIONS CONTAINING UNCOATED SILICONE ELASTOMERS AND NON SILICONE TREATED PIGMENTS

CROSS-REFERENCE TO RELATED PATENT APPLICATION

The present application is a continuation of parent patent application Ser. No. 11/410,465, filed on Apr. 25, 2006.

BACKGROUND OF THE INVENTION

Cosmetic products, and particularly pigmented cosmetic products such as foundations, are developed with the aims of matching skin tone and providing uniform coverage on the skin. Some products tend to streak upon application, fail to blend with natural skin tone, or change color during application. Other products become unstable and separate during storage, and thus require mixing before application.

SUMMARY OF THE INVENTION

A first aspect of the present invention is directed to a cosmetic composition in the form of an emulsion that contains an uncoated silicone elastomer, a solvent for the elastomer, a non-silicone treated pigment, and an emulsifier. Methods of preparing the compositions are also provided.

Another aspect of the present invention is directed to a method for applying colored make-up to a keratinous substrate, comprising applying to the substrate a cosmetic composition in the form of an emulsion that contains an uncoated silicone elastomer, a solvent for the elastomer, a non-silicone treated pigment and an emulsifier.

Applicants have discovered that inventive compositions containing an uncoated silicone elastomer were stable over a much longer period of time as compared to compositions containing a coated silicone elastomer commonly used in the cosmetics industry.

Applicants have also discovered that the bulk tone of the compositions (i.e., the skin tone of the inventive compositions in the container) is substantially identical to the skin tone (i.e., the color shade of the compositions once applied to skin). Without intending to be bound by theory, and contrary to what persons skilled in the art would have expected, Applicants believe that non-silicone treated pigments tend not to re-agglomerate during storage.

DETAILED DESCRIPTION

Silicone elastomers useful in the cosmetics industry may be coated, typically with a hard resin or micro-fine particles. Examples of coated elastomers include KSP-100, KSP-200 and KSP-300 (Shin-Etsu Silicones of America, Inc., Akron, Ohio), which are coated with a hard silicone resin, and DC9701 (Dow Corning Corp., Midland, Mich.) which is coated with micro-fine silica particles. The compositions of the present invention, however, require the presence of uncoated silicone elastomers. Applicants have discovered that uncoated silicone elastomers, even those which are considered "non-emulsifying", will form, at least in the context of the invention, a stable emulsion.

The cosmetic compositions of the present invention are emulsions, and thus contain at least two phases, namely a continuous phase and a dispersed phase. The first phase, which may be either the continuous or the dispersed phase, contains the uncoated silicone elastomer (which is hydrophobic in nature). The second phase, which can be hydrophilic or hydrophobic, is discrete from the first phase. This phase may be aqueous in nature, such that the emulsion would be an oil-in-water or water-in-oil emulsion. Alternatively, the second phase may contain immiscible oil, thus producing an oil-in-oil emulsion.

Broadly, uncoated forms of cosmetically acceptable silicone elastomers are suitable for use in the present invention. These elastomers are considered non-emulsifying e.g., they do not contain any appreciable amount of polyoxyalkylenes. In some embodiments, the uncoated silicone elastomer is a cross-linked reaction product of a polysiloxane with, for example, an alpha, omega-diene. See U.S. Pat. No. 5,654,362, incorporated herein by reference (specifically column 2, lines 2-16; 22-67 and column 6, lines 15-40 thereof), and U.S. Pat. No. 6,793,915. These uncoated silicone elastomers include cross-linked or partially cross-linked cyclomethicone (and) dimethicone crosspolymers. These elastomers may be prepared by a crosslinking reaction between (a) ≡Si—H containing polysiloxanes and (b) an alpha, omega-diene in the presence of a platinum catalyst and (c) a low molecular weight linear or cyclic polysiloxane. The elastomer can be swollen with the low molecular weight polysiloxane under a shear force. The containing polysiloxane of part (a) is represented by compounds of formula $(R^1)_3SiO(R^2_2SiO)_a(R^3HSiO)_bSi(R^1)_3$, designated herein as type $A^1$, and compounds of the formula $H(R^1)_2SiO(R^2_2SiO)_cSi(R^1)_2H$ or formula $H(R^1)_2SiO_2SiO(R^2_2SiO)_a(R^3HSiO)_bSi(R^1)_2H$, designated herein as type $A^2$. In these formulas, $R^1$, $R^2$, and $R^3$ are alkyl groups with 1-6 carbon atoms, a is 0-250, b is 1-250, and c is 0-250. The molar ratio of compounds $A^1:A^2$ is 0-20, preferably 0-5. The alpha, omega-diene in part (b) is a compound of the formula $CH_2\!=\!\!CH(CH_2)_x(CH\!=\!\!CH_2$ where x is 1-20. Representative examples of suitable alpha, omega-dienes include 1,4-pentadiene, 1,5-hexadiene, 1,6-heptadiene, 1,7-octadiene, 1,8-nonadiene, 1,9-decadiene, 1,11-dodecadiene, 1,13-tetradecadiene, and 1,19-eicosadiene. More specific examples of these uncoated silicone elastomers include DC-9040, DC-9041 and DC-9045. See U.S. Pat. No. 6,793,915, column 5, lines 9-34.

Dimethicone/vinyldimethicone crosspolymer compositions (that are cross-linked or partially cross-linked) (e.g., KSG-15 and USG-103, commercially available from Shin-Etsu Silicones of America), and cross-linked or partially cross-linked vinyldimethicone/methicone crosspolymer in cyclomethicone (e.g., GE 1229 from General Electric Silicones (Waterford, N.Y.)) may also be useful. See U.S. Pat. No. 6,793,915, column 5, lines 5-8 and 35-47. The suitability of other uncoated silicone elastomers for use in the present invention may be evaluated in accordance with standard techniques, such as described in the working examples.

Commercially available uncoated silicone elastomers such as DC-9040, DC-9041, DC-9045, KSG-15 and USG-103 are already present in the form of a gel, wherein the elastomer is formulated in a solvent such as cyclomethicone, dimethicone or another silicone oil. Thus, if the present compositions are formulated by adding the elastomer in powder form, they also require addition of a solvent for the elastomer. Volatile and non-volatile silicone oils are useful for this purpose. Suitable volatile silicone oils include linear or cyclic silicones containing from 2 to 7 silicon atoms, optionally containing alkyl or alkoxy groups containing from 1 to 10 carbon atoms e.g., cyclopentasiloxane, octamethylcyclotetrasiloxane, decamethylcyclopentasiloxane, hexadecamethylcyclohexasiloxane, heptamethylhexyltrisiloxane and heptamethyloctyltrisiloxane, and mixtures thereof.

Examples of suitable non-volatile silicone oils include linear polydimethylsiloxanes (PDMSs) that are liquid at room temperature; polydimethylsiloxanes that may be substituted with fluoro groups, functional groups such as hydroxyl, thiol or amine groups, aliphatic (e.g., alkyl) groups or aromatic (e.g., phenyl) groups, which are pendent and/or at the end of a silicone chain, these groups each containing from 2 to 24 carbon atoms; phenylsilicones, for instance phenyltrimethicones, phenyldimethicones, trimethyl pentaphenyl trisiloxane (e.g., DC555 from Dow Corning), tetramethyl tetraphenyltrisiloxane, phenyl trimethylsiloxydiphenylsiloxanes, diphenyl dimethicones, diphenyl methyldiphenyl trisiloxanes and 2-phenylethyl trimethylsiloxysilicates. Other examples of silicone oils include polysiloxanes modified with fatty acids, fatty alcohols or polyoxyalkylenes, fluorosilicates and perfluoro oils.

The uncoated silicone elastomer is present in an amount that generally ranges from about 0.1% to about 35%, and in some embodiments, from about 0.1% to about 25%, and yet other embodiments from about 0.1% to about 15%, wherein all percentages are based on the dry weight of the elastomer (i.e., in powder form) relative to the total weight of the cosmetic composition. In some other embodiments, the amount of uncoated silicone elastomer is about 5.6% of the total weight of the composition. Relatively high amounts of the elastomer may be present. In some embodiments, coated silicone elastomers may be present, e.g., in amounts up to 50% based on total weight of the composition, provided that the stability of the emulsion is not compromised.

Pigments suitable for use in the present invention are treated e.g., coated or surrounded, with a non-silicone compound. By "silicone compound" it is meant any compound that contains silicone e.g., silicones, silanes and siloxanes. The treated pigment is more hydrophobic than the untreated pigments. Amino acid-treated pigments are useful in the practice of the present invention. Examples of amino acids include N-acylamino acid salts of glycine, alanine, valine, leucine, isoleucine, phenylalanine, proline, threonine, serine, arginine, histidine, lysine, aspartic acid and glutamic acid, and salts thereof. Specific examples include N-acyl-N-methylglycine, N-acyl-N-methyl-$\beta$-alanine and N-acyl-L-glutamine acid and in some embodiments, the Al, Mg, Ca, Zn, Zr and Ti salts thereof. The acyl group may include a residue of capric acid, lauric acid, myristic acid, palmitic acid, stearic acid or oleic acid. See U.S. Pat. No. 4,606,914, incorporated herein by reference (specifically, column 3, lines 1-31 thereof), and U.S. Pat. No. 6,296,860. Methods of treating pigments with amino acids are also disclosed in the '914 patent. Treated pigments may further include pigments treated with a vegetable-derived amino acid such as titanium dioxide coated with disodium stearoyl glutamate and aluminum hydroxide (e.g., NAI, commercially available from U.S. Cosmetics Corp., a distributor of Miyoshi Kasei (Japan)).

Additional examples of treated pigments suitable for use in the present invention include pigments treated with perfluoro compounds (cosmetically acceptable organic fluoro compounds) such as C9-C15 (i.e., C9, C10, C11, C12, C13, C14 and C15) fluoroalcohol phosphates.

Further examples of treated pigments suitable for use in the present invention include titanate-treated pigments. Examples of these pigments include coordinate titanates and monoalkoxy titanates such as monoalkoxy triacyl titanates (also referred to as monoalkyl titanates). See, U.S. Patent Application Publication No. 20050019284 (specifically paragraphs [0038]-[0052]). Specific examples of titanates include isopropyl triisostearoyl titanate (ITT, available from KOBO, South Plainfield, N.J.), isopropyl dimethacryl isostearoyl titanate, and isopropyl dimethacryl isostearoyl titanate.

Further examples of treated pigments that may be useful in the present invention are described in U.S. Pat. No. 5,167,709 (pigments treated with a polyvalent salt of an amidosulfonic acid) and U.S. Pat. No. 5,928,658 (pigments treated with water-soluble metal salts of fatty acids, hydrogenated lecithin or acyl collagen). The suitability of other treated pigments for use in the present invention may be evaluated in accordance with standard techniques, such as described in the working examples.

A plurality of treated pigments of different color (or shades of color) may be present in the composition in order to achieve the desired color or tone.

The pigments that may be treated include white pigments, colored pigments, inorganic pigments, pigments having a micron size and pigments not having a micron size. Among the inorganic pigments that may be useful are titanium dioxide, iron oxide, zirconium oxide, zinc oxide, cerium oxide, chromium oxide, manganese violet, ultramarine blue, chromium hydrate, and ferric blue.

Broadly, the amount of pigment may vary widely, provided that it does not interfere with the formation or stability of the emulsion, and provides the desired coverage, tone and color when applied to the skin—determinations which are within the level of skill in the art. The amount of the treated pigment generally ranges from about 0% to about 70%, and in some embodiments from about 0% to about 35%, and in some other embodiments from about 0% to about 20%, based on the total weight of the cosmetic composition. In some other embodiments, the amount of the treated pigment is about 10% of the total weight of the composition. As used herein, the term "about 0%" when referring to an ingredient that is stated to be present in an embodiment of the invention, means a finite amount greater than zero.

Emulsifiers typically employed in the compositions of the present invention include anionic, nonionic and cationic emulsifiers. See, e.g., *Encyclopedia of Chemical Technology*, KIRK-OTHMER, volume 22, pp. 333-432, 3rd edition, 1979, Wiley, for the definition of the properties and (emulsifying) functions of the emulsifiers, in particular pp. 347-377 of this publication regarding anionic and nonionic emulsifiers. Examples of nonionic emulsifiers useful in the compositions of the invention include fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters, and ethoxylated compounds such as Polysorbate-20, Laureth-7, Laureth-4 and Sepigel® 305. Examples of anionic emulsifiers include $C_{16}$-$C_{30}$ fatty acids neutralized by amines, ammonia or the alkali metal salts thereof. Examples of cationic emulsifiers include quaternary amines, amine oxides and amines, e.g., alkyl amines, alkyl imidazolines, ethoxylated amines, quaternary compounds, and quaternized esters. Cationic emulsifiers may also provide a conditioning effect.

Organosilicone emulsifiers are particularly useful, particularly in embodiments wherein the emulsion is a water-in-oil (silicone) emulsion. Such emulsifiers include silicone polyethers and polyalkoxylated silicone elastomers.

Silicone polyethers contain oxyethylene units of the formula $CH_2CH_2O$, e.g., such as described in U.S. Pat. No. 4,268,499, column 5, lines 1-16, U.S. Patent Application Publication No. 2002/0028223, paragraph [0098] and U.S. Patent Application Publication No. 2003/0049212, paragraphs [0160]-[0167]. Examples of silicone polyethers include PEG/PPG-18/18 Dimethicone, available as a blend with cyclopentasiloxane as DC5225C or DC5185, PEG-9 Dimethicone, available as KF6017 or KF6028 from Shin- Etsu, cetyl dimethicone copolyol-polyglyceryl-4-isostearate-hexylaurate available as ABIL® WE 09 from Goldschmidt Chemical Corporation, Hopewell, Va., Cetyl Dimethicone Copolyol (ABIL® EM 90), (ABIL® EM 97), Laurylmethicone Copolyol (5200), Cyclomethicone (and) Dimethicone Copolyol available as DC 3225 C from Dow Corning, and Cyclopentasiloxane and Dimethicone Copolyol available as GE SF 1528 from GE Silicones.

Polyalkoxylated silicone elastomers are cross-linked organopolysiloxanes that contain at least one residue such as a polyoxyalkylene residue. The polyoxyalkylene residue may be pendant such as in the case of KSG-210 from Shin-Etsu, or may be the crosslinking agent, such as in the case of KSG-710, also from Shin-Etsu. Examples of polyalkoxylated silicone elastomers are described in U.S. Patent Application No. 2005/0053571, paragraphs [0055]-[0061].

The amount of emulsifier generally ranges from about 0% to about 20% by weight, and in some embodiments from about 0% to about 10%, based on the total weight of the cosmetic composition. In some embodiments, the amount of emulsifier is about 2% of the total weight of the composition.

The inventive compositions may contain a cosmetically or dermatologically acceptable and, in general, physiologically acceptable oil, such as carbon-based, hydrocarbon-based, fluoro and/or silicone oils, of mineral, animal, plant or synthetic origin, alone or as a mixture. Volatile oils and/or nonvolatile oils may be present. The oil(s), if present, constitutes a hydrophobic phase.

Representative volatile oils include non-polar volatile hydrocarbon-based oils (which as used herein, refers to oil containing only hydrogen and carbon atoms), silicone oils (optionally comprising alkyl or alkoxy groups that are pendant or at the end of a silicone chain), and fluoro oils. Suitable hydrocarbon-based oils include isoparaffins, i.e., branched alkanes containing 8-16 carbon atoms, such as isododecane (also known as 2,2,4,4,6-pentamethylheptane), and petroleum distillates.

Examples of nonvolatile oils suitable for use in the cosmetic sticks of the invention include esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octildodecanol, and fatty alcohols such as oleyl alcohol, isocetyl alcohol, and the like.

The inventive compositions may contain water and/or water-miscible solvents such as glycols (glycols containing from 2 to 8 carbon atoms, such as propylene glycol, ethylene glycol, butylene glycol, dipropylene glycol and pentylene glycol), in which case the emulsions have an aqueous phase. In these embodiments, the amount of water (and/or glycol) present ranges generally from about 0% to about 90%, and in some embodiments from about 5% to about 60%, based on the total weight of the cosmetic composition.

The cosmetic compositions of the present invention may be liquid (e.g., milks, creams, gels, ointments, mousses or lotions), or substantially solid (e.g., compressed powders and sticks). They may be applied to keratinous substrates (tissue or synthetic), particularly skin. The cosmetic composition may be in the form of foundations, concealers, blushes, rouges, lipsticks, lip stains, lip glosses, mascaras, eyeshadows and eyeliners.

Accordingly, the cosmetic compositions may further contain at least one other cosmetically acceptable ingredient, including active agents and additives alike. Examples of such ingredients include other solvents, structuring agents such as waxes and polymers, hydrophobic (lipophilic) and hydrophilic thickeners or gelling agents, skin conditioning agents (humectants, exfoliants or emollients), dispersion enhancing agents, fillers (e.g., powders and mother-of-pearl), fibers, sunscreen agents (e.g., octocrylene, octinoxate, avobenzone), preservatives (e.g., sodium citrate, phenoxyethanol, parabens and mixtures thereof), chelators (such as EDTA and salts thereof, particularly sodium and potassium salts), antioxidants (e.g., BHT, tocopherol), neutralizing or pH-adjusting agents (e.g., sodium hydroxide), and cosmetically active agents and dermatological active agents such as, for example, additional skin care actives such as peptides (e.g., Matrixyl [pentapeptide derivative]), farnesol, bisabolol, phytantriol, vitamins and derivatives thereof such as ascorbic acid, vitamin A (e.g., retinoid derivatives such as retinyl palmitate or retinyl propionate), vitamin E (e.g., tocopherol acetate), vitamin $B_3$ (e.g., niacinamide) and vitamin $B_5$ (e.g., panthenol), anti-acne agents (resorcinol and salicylic acid), antioxidants (e.g., phytosterols and lipoic acid), flavonoids (e.g., isoflavones, phytoestrogens), and agents suitable for aesthetic purposes such as essential oils, fragrances, skin sensates, opacifiers, aromatic compounds (e.g., clove oil, menthol, camphor, eucalyptus oil, and eugenol), anti-inflammatory agents, defoaming agents, and essential fatty acids.

Other solvents include lower monoalcohols (e.g., ethanol and isopropyl alcohol), $C_3$-$C_4$ ketones and $C_2$-$C_4$ aldehydes.

The compositions may contain a wax, such as in the case of mascara. Suitable waxes include waxes of animal origin, waxes of plant origin, waxes of mineral origin and waxes of synthetic origin. For the purposes of the present invention, the term "wax" means a lipophilic fatty compound that is solid at room temperature (25° C.) and atmospheric pressure (760 mmHg, i.e., $10^5$ Pa), which undergoes a reversible solid/liquid change of state and which has a melting point of greater than 30° C. and in some embodiments, greater than 55° C. up to 120° C. or even as high as 200° C.

Examples of waxes of animal origin include beeswaxes, lanolin waxes and Chinese insect waxes. Examples of waxes of plant origin include rice waxes, carnauba wax, candellila wax, ouricurry wax, cork fibre waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes. Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils. The wax may be present in the compositions in an amount generally ranging from about 0% to about 50%, based on the total weight of the composition.

The compositions of the present invention may contain polymers, e.g., film forming polymers that are compatible with the other ingredients and form a film after application. Suitable polymers include polyvinylpyrrolidones (PVP) and vinyl copolymers, e.g., vinyl pyrrolidone (VP)/hexadecane copolymer, PVP/hexadecene copolymer and VP/eicosene copolymer (e.g., Ganex V220, which is a tradename of ISP Inc. of Wayne, N.J.), trimethylsiloxysilicate and acrylates copolymer. The polymer may be present in the compositions in an amount generally ranging from 0% to about 35% by weight.

Examples of lipophilic thickeners or gelling agents include modified clays such as hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox, hydrophobic silica, such as fumed silica, metal salts of fatty acids and polyethylene.

Water-soluble or hydrophilic thickeners or gelling agents that may be used include carboxyvinyl polymers, such as polyvinylpyrrolidone (PVP) and polyvinyl alcohol, crosslinked acrylates (e.g. Carbopol 982), hydrophobically-modified acrylates (e.g. Carbopol 1382); polyacrylamides such as the crosslinked copolymers sold under the names Sepigel 305 (CTFA name: polyacrylamide/$C_{13}$-$C_{14}$ isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose, polysaccharides and natural gums such as xanthan gum, sclerotium, carrageenan and pectin, polysaccharide resins such as starch and its derivatives, and hyaluronic acid and its salts.

The amount of thickener or gelling agent generally ranges from about 0% to about 10%, based on the total weight of the cosmetic composition.

Compositions of the present invention may also contain a skin conditioning agent (such as a humectants, exfoliant or emollients). Examples of such agents include sodium lactate, mannitol, amino acids, hyaluronic acid, lanolin, urea, petroleum jelly and mixtures thereof. Other examples include polyols such as glycerin, diglycerin, triglycerin, polyglycerin, polyethylene glycol and sorbitol. The $C_2$-$C_8$ glycols disclosed herein are also useful in this respect. These agents are present in the compositions of the present invention in amounts generally ranging from about 0.1% to about 20%, based on the total weight of the cosmetic composition.

Of course, compositions of the present invention may be applied by hand. Alternatively, or in conjunction therewith, they may be applied via an applicator such as sponges, cotton, brushes and puffs of natural or synthetic materials. In addition, the applicator may be attached to a container, said container serving as a reservoir for the cosmetic composition.

The following examples are intended to further illustrate the present invention. They are not intended to limit the invention in any way. Where trade names for various ingredients are given, the percentage indicated reflects the weight used of the ingredient as it comes from the manufacturer and not just the active component in that ingredient.

EXAMPLES

The following examples disclose two inventive and two comparative emulsions, all of which are in the form of a cosmetic foundation. Each of the examples was prepared in accordance with the following procedure.

The main preparation kettle is sanitized with deionized (DI) water (rinse for 30 minutes with DI water heated to 90° C.). The rest of the procedure is carried out at 25° C. Into the main kettle, phases A1 and A3 are combined and mixed for 20 minutes, until the bentone is completely dispersed. Phase A2 ingredients are then added to the A1/A3 mixture and mixed until A2 is completely dispersed within A1/A3, and a smooth texture is achieved. In a separate kettle, the Phase B ingredients are mixed until uniform. The contents of the second kettle are then added to the main kettle and mixed until an emulsion is formed.

The stability of each of the resulting foundations was determined by using standard techniques such as freeze/thaw cycles, centrifugation, and storage at varying temperatures and times.

The stability of the pigments within the emulsion was determined by observing whether the skin tone changed upon application of the product to the skin.

Example 1

Inventive Foundation

| Sequence | Trade Name | CTFA Name | % wt/wt |
|---|---|---|---|
| A1 | Dow Corning 245 fl | Cyclopentasiloxane | 15.00 |
| | Wickenol 153 | Isotridecyl Isononanoate | 7.50 |
| | Bentone 38VCG | Disteardimonium hectorite | 1.00 |
| | KF-6028 | PEG-9 Polydimethylsiloxyethyl dimethicone | 2.00 |
| A2 | DC 9045 | Dimethicone Crosspolymer and Cyclopentasiloxane | 44.50 |
| A3 | NAI-TAO-77891 | $TiO_2$ & Disodium Stearoyl Glutamate & Aluminum Hydroxide | 8.55 |
| | NAI-C33-8073-10 | YELLOW Iron Oxides & Disodium Stearoyl Glutamate & Aluminum Hydroxide | 1.00 |
| | NAI-C33-8075-10 | RED Iron Oxides & Disodium Stearoyl Glutamate & Aluminum Hydroxide | 0.37 |
| | NAI-C33-134-10 | Black Iron Oxides & Disodium Stearoyl Glutamate & Aluminum Hydroxide | 0.08 |
| B | DI Water | DI water | 14.00 |
| | Sodium Citrate | Sodium Citrate | 0.20 |
| | Phenonip | Phenoxyethanol, Methylparaben, Butylparaben Ethylparaben, Propylparaben, Isobutylparaben | 0.80 |
| | Glycerin | Glycerin | 5.00 |

The foundation was stable and did not change skin tone upon application to the skin.

Example 2

Inventive Foundation

| Sequence | Trade Name | CTFA Name | % wt/wt |
|---|---|---|---|
| A1 | Dow Corning 245 fl | Cyclopentasiloxane | 15.00 |
|  | Wickenol 153 | Isotridecyl Isononanoate | 7.50 |
|  | Bentone 38VCG | Disteardimonium hectorite | 1.00 |
|  | KF-6028 | PEG-9 Polydimethylsiloxyethyl dimethicone | 2.00 |
| A2 | DC 9045 | Dimethicone Crosspolymer and Cyclopentasiloxane | 44.50 |
| A3 | TITANIUM DIOXIDE CR-50-PF-5 | C9-15 fluoroalcohol treated titanium dioxide | 8.55 |
|  | PF-5 YELLOW 601 | C9-15 fluoroalcohol treated yellow iron oxide | 1.00 |
|  | PF-5 RED R 516 L | C9-15 fluoroalcohol treated red iron oxide | 0.37 |
|  | PF-5 BLACK BL-100 | C9-15 fluoroalcohol treated black iron oxide | 0.08 |
| B | DI Water | DI water | 14.00 |
|  | Sodium Citrate | Sodium Citrate | 0.20 |
|  | Phenonip | Phenoxyethanol, Methylparaben, Butylparaben Ethylparaben, Propylparaben, Isobutylparaben | 0.80 |
|  | Glycerin | Glycerin | 5.00 |

The foundation was stable and did not change skin tone upon application to the skin.

Example 3

Comparative Foundation Containing Silicone Treated Pigments

| Sequence | Trade Name | CTFA Name | % wt/wt |
|---|---|---|---|
| A1 | Dow Corning 245 fl | Cyclopentasiloxane | 15.00 |
|  | Wickenol 153 | Isotridecyl Isononanoate | 7.50 |
|  | Bentone 38VCG | Disteardimonium hectorite | 1.00 |
|  | KF-6028 | PEG-9 Polydimethylsiloxyethyl dimethicone | 2.00 |
| A2 | DC 9045 | Dimethicone Crosspolymer and Cyclopentasiloxane | 44.50 |
| A3 | RBTD-11S2 | TiO$_2$ with triethoxy Caprylylsilane | 7.70 |
|  | BGYO-11S2 | Iron oxide with triethoxy Caprylylsilane | 1.44 |
|  | BGRO-11S2 | Iron oxide with triethoxy Caprylylsilane | 0.56 |
|  | BGBO-11S2 | Iron oxide with triethoxy Caprylylsilane | 0.30 |
| B | DI Water | DI water | 14.00 |
|  | Sodium Citrate | Sodium Citrate | 0.20 |
|  | Phenonip | Phenoxyethanol, Methylparaben, Butylparaben Ethylparaben, Propylparaben, Isobutylparaben | 0.80 |
|  | Glycerin | Glycerin | 5.00 |

In direct contrast to the inventive foundations disclosed in examples 1 and 2, the comparative foundation containing silane-treated pigments was observed to change skin tone when it was applied to the skin.

Example 4

Comparative Foundation Containing Coated Silicone Elastomer

| Sequence | Trade Name | CTFA Name | % wt/wt |
|---|---|---|---|
| A1 | Dow Corning 245 fl | Cyclopentasiloxane | 56.44 |
|  | Wickenol 153 | Isotridecyl Isononanoate | 1.00 |
|  | Parsol MCX | Octinoxate | 7.50 |
|  | Bentone 38VCG | Disteardimonium hectorite | 1.00 |
|  | KF-6012 | PEG 10 Dimethicone | 0.45 |
|  | KF-6028 | PEG-9 Polydimethylsiloxyethyl dimethicone | 2.00 |
| A2 | KSP 100 | Vinyldimethicone/methicone silsesquioxane crosspolymer | 5.56 |
| A3 | NAI-TAO-77891 | TiO$_2$ & Disodium Stearoyl Glutamate & Aluminum Hydroxide | 0.78 |
|  | NAI-C33-8073-10 | YELLOW Iron Oxides & Disodium Stearoyl Glutamate & Aluminum Hydroxide | 4.01 |
|  | NAI-C33-8075-10 | RED Iron Oxides & Disodium Stearoyl Glutamate & Aluminum Hydroxide | 1.43 |
|  | NAI-C33-134-10 | BLACK Iron Oxides & Disodium Stearoyl Glutamate & Aluminum Hydroxide | 1.28 |
| B | DI Water | DI water | 12.55 |
|  | Sodium Citrate | Sodium Citrate | 0.20 |
|  | Phenonip | Phenoxyethanol, Methylparaben, Butylparaben Ethylparaben, Propylparaben, Isobutylparaben | 0.80 |
|  | Glycerin | Glycerin | 5.00 |

In direct contrast to the inventive foundations disclosed in examples 1 and 2, the comparative foundation containing a coated silicone elastomer but without uncoated silicone elastomer, was observed to separate immediately upon centrifugation, or after 1 day of storage at various temperatures.

All publications cited, in the specification, both patent publications and non-patent publications are indicative of the level of skill of those skilled in the art to which this invention pertains. Any publication not already incorporated by reference herein is herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. A cosmetic composition in the form of an emulsion comprising:
   i) a non-emulsifying, uncoated silicone elastomer, wherein said non-emulsifying, uncoated silicone elastomer is a dimethicone crosspolymer;

ii) a solvent for said elastomer;

iii) at least one non silicone treated pigment chosen from the group consisting of an amino acid-treated pigment, a perfluoro-treated pigment and a monoalkoxy triacyl titanate-treated pigment; and iv) an emulsifier, with the proviso that the cosmetic composition is free of any peptide and free of pigments treated with a silicone compound.

2. The cosmetic composition of claim 1, wherein said solvent is selected from the group consisting of cyclopentasiloxane, dimethicone, polydimethylsiloxanes, phenyltrimethicone, and trimethyl pentaphenyl trisiloxane.

3. The cosmetic composition of claim 1, wherein the cosmetic composition comprises about 0.1% to about 15% of said non-emulsifying, uncoated silicone elastomer based on the total weight of said composition.

4. The cosmetic composition of claim 1, wherein said pigment is an amino acid-treated pigment.

5. The cosmetic composition of claim 4, wherein said amino acid-treated pigment is an N-acyl-glutamine-treated pigment.

6. The cosmetic composition of claim 4, wherein said amino acid-treated pigment is a disodium stearoyl glutamate-treated pigment.

7. The cosmetic composition of claim 1, wherein said at least one pigment is a perfluoro-treated pigment.

8. The cosmetic composition of claim 7, wherein said perfluoro-treated pigment is a pigment treated with a C9-C15 fluoroalcohol phosphate.

9. The cosmetic composition of claim 1, wherein said at least one pigment is a monoalkoxy triacyl titanate-treated pigment.

10. The cosmetic composition of claim 9, wherein said monoalkoxy triacyl titanate-treated pigment is an isopropyl triisostearoyl titanate-treated pigment.

11. The cosmetic composition of claim 1, which comprises more than one treated pigment, each of which has a different color.

12. The cosmetic composition of claim 1, wherein said at least one pigment comprises an iron oxide, a dioxide or an iron oxide and a dioxide.

13. The cosmetic composition of claim 12, wherein said dioxide is titanium dioxide, and said iron oxide is yellow iron oxide, black iron oxide, red iron oxide or a mixture thereof.

14. The cosmetic composition of claim 1, wherein said emulsifier is a silicone polyether.

15. The cosmetic composition of claim 1, wherein said emulsifier is a polyalkoxylated silicone elastomer.

16. The cosmetic composition of claim 1, further comprising water and/or a water-miscible solvent.

17. The cosmetic composition of claim 1, further comprising a non-volatile oil.

18. The cosmetic composition of claim 1, further comprising a sunscreen agent.

19. The cosmetic composition of claim 1, wherein the cosmetic composition is in the form of a foundation.

20. A method of applying make-up to a keratinous substrate, comprising applying to the substrate a cosmetic composition according to claim 1.

21. The method of claim 20, wherein the substrate is skin.

22. A cosmetic composition in the form of an emulsion comprising:

i) a non-emulsifying, uncoated silicone elastomer, wherein said non-emulsifying, uncoated silicone elastomer a dimethicone crosspolymer;

ii) a solvent for said elastomer selected from the group consisting of cyclopentasiloxane, dimethicone, polydimethylsiloxanes, phenyltrimethicone, and trimethyl pentaphenyl trisiloxane;

iii) a pigment treated with a C9-C15 fluoroalcohol phosphate, wherein the pigment is an iron oxide pigment, iron dioxide pigment, or an iron oxide and dioxide pigment; and iv) an emulsifier selected from the group consisting of a polyalkoxylated silicone elastomer and a silicone polyether;

with the proviso that the cosmetic composition is free of any peptide and free of pigments treated with a silicone compound.

23. The cosmetic composition of claim 20, wherein ii) the solvent for said elastomer is selected from the group consisting of cyclopentasiloxane and dimethicone;

iii) the at least one non silicone treated pigment is an amino acid treated pigment; and iv) the emulsifier is selected from the group consisting of a polyalkoxylated silicone elastomer and a silicone polyether.

24. The cosmetic composition of claim 23, further comprising glycerin.

* * * * *